United States Patent
Son et al.

(10) Patent No.: US 9,412,159 B2
(45) Date of Patent: Aug. 9, 2016

(54) METHOD FOR INSPECTING FLAT PANEL

(75) Inventors: Jai-Ho Son, Gwangju (KR); Hyun-Min Lee, Daejeon (KR); Min-Gu Kang, Daejeon (KR); Sang-Yoon Lee, Daejeon (KR); Ssang-Gun Lim, Daejeon (KR)

(73) Assignee: INTEKPLUS CO., LTD., Daejeon (KR)

( * ) Notice: Subject to any disclaimer, the term of this patent is extended or adjusted under 35 U.S.C. 154(b) by 210 days.

(21) Appl. No.: 14/343,345

(22) PCT Filed: Sep. 13, 2012

(86) PCT No.: PCT/KR2012/007352
§ 371 (c)(1),
(2), (4) Date: Mar. 6, 2014

(87) PCT Pub. No.: WO2013/039340
PCT Pub. Date: Mar. 21, 2013

(65) Prior Publication Data
US 2014/0226004 A1    Aug. 14, 2014

(30) Foreign Application Priority Data
Sep. 15, 2011    (KR) .................. 10-2011-0093102

(51) Int. Cl.
*H04N 7/18*    (2006.01)
*G06T 7/00*    (2006.01)
(Continued)

(52) U.S. Cl.
CPC .............. *G06T 7/0004* (2013.01); *G01N 21/95* (2013.01); *H04N 7/18* (2013.01); *G01N 2021/9513* (2013.01); *G02F 1/1309* (2013.01); *G06T 2207/30121* (2013.01)

(58) Field of Classification Search
CPC .......... G01N 2021/9513; G01N 21/95; G01N 21/956; G01N 21/9501; G01N 21/892; G06T 2207/30121; G06T 7/0004; G06K 9/3216
USPC .................................................... 348/92, 345
See application file for complete search history.

(56) References Cited

U.S. PATENT DOCUMENTS 7,538,815 B1 *   5/2009   Belikov ................... G02B 7/36
                                                      348/345
7,817,264 B2 *  10/2010   Sanada ............... G01N 21/9501
                                                      356/237.3
(Continued)

FOREIGN PATENT DOCUMENTS

CN          1232767 A       10/1999
CN          1438469 A        8/2003
(Continued)

*Primary Examiner* — Sath V Perungavoor
*Assistant Examiner* — Nathnael Aynalem
(74) *Attorney, Agent, or Firm* — Novick, Kim & Lee, PLLC; Jae Youn Kim

(57) ABSTRACT

Disclosed is a method for inspecting a flat panel. The method for inspecting the flat panel includes the steps of: arranging a camera at a measurement location of the flat panel by horizontally moving at least one of the flat panel and the camera; automatically focusing the camera with respect to a measuring target of the flat panel at the measurement location; acquiring a plurality of images for the measuring target by vertically moving the focused camera within a set region on the basis of the present location of the camera when focusing the camera; selecting the image having the most definition for the measuring target among the acquired images; processing the selected image; and determining whether the measuring target is defective or not.

3 Claims, 2 Drawing Sheets

(51) Int. Cl.
*G01N 21/95* (2006.01)
*G02F 1/13* (2006.01)

(56) References Cited

U.S. PATENT DOCUMENTS

| | | | | |
|---|---|---|---|---|
| 2001/0002462 | A1* | 5/2001 | Kosuge | G01B 11/024 702/167 |
| 2003/0048439 | A1* | 3/2003 | Yoshida | G01N 21/95684 356/237.5 |
| 2004/0070753 | A1 | 4/2004 | Sugihara et al. | |
| 2004/0090589 | A1* | 5/2004 | Jung | G02F 1/1339 349/187 |
| 2004/0111230 | A1* | 6/2004 | Kosuge | G06K 9/3216 702/94 |
| 2005/0254045 | A1* | 11/2005 | Weiss | G01N 21/95 356/237.5 |
| 2007/0160283 | A1* | 7/2007 | Saphier | G06K 9/033 382/152 |
| 2010/0067780 | A1* | 3/2010 | Kawaragi | B81C 99/005 382/149 |
| 2011/0255770 | A1* | 10/2011 | Touya | G06T 7/001 382/144 |

FOREIGN PATENT DOCUMENTS

| | | |
|---|---|---|
| CN | 1510393 A | 7/2004 |
| CN | 1648645 A | 8/2005 |
| CN | 1220032 C | 9/2005 |
| CN | 1703071 A | 11/2005 |
| JP | 09-096513 | 4/1997 |
| JP | 2004-061289 | 2/2004 |
| JP | 4008168 B2 | 11/2007 |
| JP | 2011-082506 | 4/2011 |
| KR | 10-0521016 | 10/2005 |
| KR | 10-2010-0124742 | 11/2010 |
| TW | 200933134 A | 8/2009 |
| TW | 201000885 A | 1/2010 |
| TW | 201033606 A | 9/2010 |

* cited by examiner

METHOD FOR INSPECTING FLAT PANEL

TECHNICAL FIELD

The following description relates to a method for inspecting a flat panel, and more particularly to a method for inspecting a pixel circuit pattern.

BACKGROUND ART

A liquid crystal display (LCD), which is a type of flat panels, has features of operating at low voltage with low power consumption, and displaying full range of colors with a compact size. The LCD has been increasingly used in wider applications ranging from watches, calculators, PC monitors, and laptops, to TVs, monitors for aviation, personal portable devices, and mobile phones.

Such an LCD panel includes two glass substrates, upon which a color filter and a thin film transistor (TFT) are formed, and a liquid crystal filled between the two glass substrates. The thin film transistor, which is a circuit where a semiconductor film is formed onto a glass substrate, adjusts a liquid crystal, and controls a pixel, which is a minimum unit constituting an image. A color filter is formed by coating pixels of three colors, red (R), green (G), and blue (B), on a glass substrate, and functions to generate images.

Various quality inspections are performed after such LCD panels are manufactured, among which one important inspection is a test for circuit patterns formed in each pixel, for example, a check for any defects by measuring dimensions, such as line widths of an electrode line and a signal line of a TFT, or circuit pattern widths. Measuring line widths is important, as line widths have an impact on adhesive strength and electrical resistance values, which affect performance of each pixel.

A conventional method of measuring line widths is performed as follows: a photographing apparatus, such as a camera, is moved to a measurement position of an LCD panel to photograph images of pixel circuit patterns; and the photographed image are input to a measurement control unit, which then processes the input images to measure pixel circuit patterns.

In the LCD panel, pixels of three colors, red (R), green (G), and blue (B), are combined to generate full-color images. As pixels have different wavelength bands depending on its colors, a problem occurs in that while a clear image may be obtained for pixels of one color, images for pixels of other colors may be less clear. In addition, image qualities may be different depending on measurement locations due to a minute curve in a glass substrate.

For this reason, a method of photographing images by adding automatic focus module to a camera is used, in which pixels are focused automatically for each color. However, clear images for every pixel cannot be acquired easily due to repeatability limitations of the automatic focus module. Further, as resolution of LCD panels becomes higher, and a circuit pattern of each pixel is miniaturized, line widths may not be measured accurately by only using an automatic focus module. Regarding an apparatus for measuring line widths, Korean Patent Publication No. 10-0521016 (published on Jul. 28, 2003) discloses such an apparatus.

DISCLOSURE

Technical Problem

An object of the present disclosure is to provide a method for inspecting a flat panel, which enhances accuracy of determining a defect in a target to be measured.

Technical Solution

According to an exemplary embodiment, there is disclosed a method for inspecting a flat panel, the method includes: arranging a camera at a measurement location of the flat panel by horizontally moving at least one of the flat panel and the camera; automatically focusing the camera on a target to be measured of the flat panel at the measurement location; acquiring a plurality of images of the target to be measured by vertically moving the focused camera within a set region based on the current location of the camera; selecting an image with the highest definition among the plurality of acquired images to process the selected image; and determining whether the target to be measured is defective or not.

Effect of the Invention

In the method for inspecting a flat panel, after a camera is automatically focused on a target to be measured, images are acquired by vertically moving the camera within a set region, and among the acquired images, only an image with the highest definition is extracted to be used. As a result, accuracy of determining a defect in a target to be measured may be further enhanced, in contrast to a case in which a defect is determined by using images captured when a camera is only automatically focused without being moved.

MODES OF THE INVENTION

Figure 1:
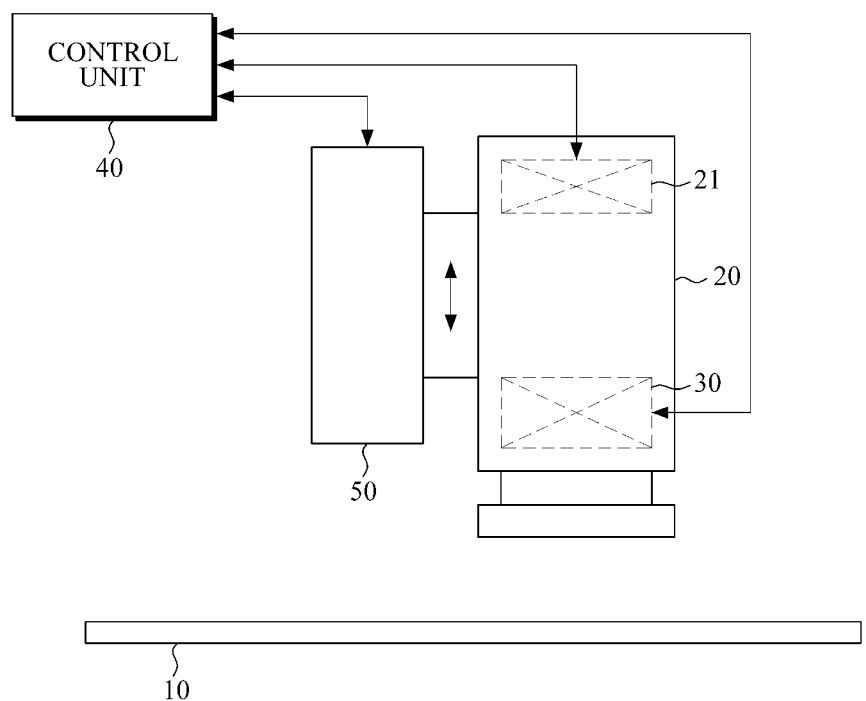
FIG. 1 is a block diagram illustrating an example of an inspecting device, which is operated by a method for inspecting a flat panel according to an exemplary embodiment.

The invention is described more fully hereinafter with reference to the accompanying drawings, in which exemplary embodiments of the invention are shown. First, when adding reference numerals to elements of the drawings, it should be noted that like reference numerals are used for like elements if possible although like elements are shown in different drawings. In addition, in the description of the present invention, if it is determined that a detailed description of commonly-used configurations or functions related to the invention may unnecessarily obscure the subject matter of the invention, the detailed description will be omitted. In the drawings, the shape and size of elements in the drawings may be exaggerated for clarity.

Hereinafter, the method for inspecting a flat panel will be described in detail with reference to the accompanying drawings.

FIG. 1 is a block diagram illustrating an example of an inspecting device, which is operated by a method for inspecting a flat panel according to an exemplary embodiment. Further, FIG. 2 is a view illustrating an example method for acquiring images with a camera at a measurement location according to the exemplary embodiment in FIG. 1.

Figure 2:
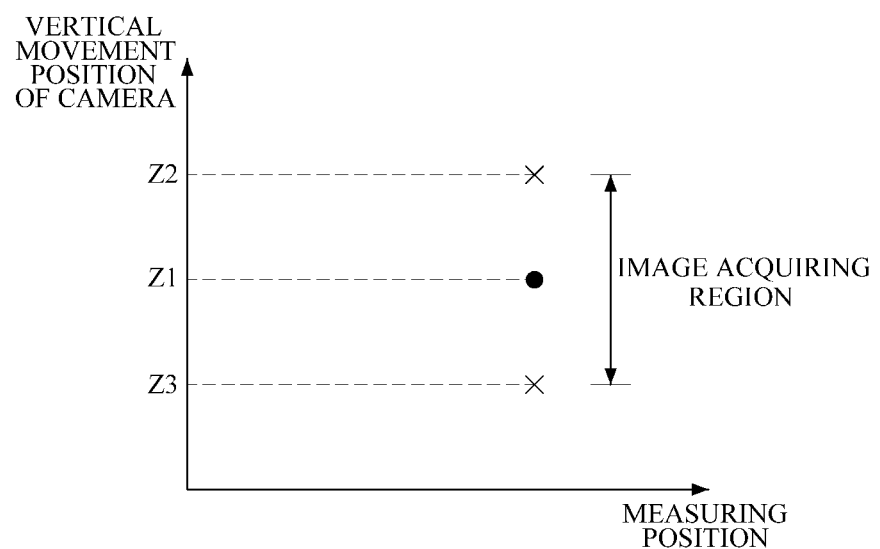
FIG. 2 is a view illustrating an example method for acquiring images with a camera at a measurement location according to the exemplary embodiment in FIG. 1.

Referring to FIGS. 1 and 2, the method for inspecting a flat panel according to an exemplary embodiment is performed as follows:

First, at least one of a flat panel 10 and a camera 20 is horizontally moved to arrange the camera 20 at a measurement location of the flat panel 10. Here, the flat panel 10 may be an LCD panel, etc. The camera 20 may be a Charge-Coupled Device (CCD) camera, etc.

For example, in order to arrange the camera 20 at a measurement location of the flat panel 10, the camera 20 may be horizontally moved with respect to the flat panel 10. With a horizontal plane defined as an X-Y plane, the camera 20, which is not shown, may be moved in an X axis and/or Y axis direction by an X axis driving device and a Y axis driving device, so as to be arranged at a desired measurement location in the flat panel 10. In another example, the flat panel 10 may be horizontally moved by X-Y stages, etc. with respect to the camera 20, or otherwise, both of the camera 20 and the flat panel 10 may be horizontally moved.

After the camera is arranged at a measurement location of the flat panel 10, the camera 20 is automatically focused on a target to be measured of the flat panel 10. Here, an automatic focusing method may be a Through The Lens (TTL) method, which uses light coming through an imaging lens.

For example, light coming through a lens system of an automatic focusing module 30 is converted by an image sensor 21, such as a CCD, into an electric signal to be input to a control unit 40, which then generates images from the input electric signal. The control unit 40 detects, from image information, whether a camera is focused on a target to be measured by using a contrast detection method, a phase difference detection method, etc. In response to a determination by the control unit 40 that the camera is not focused on the target to be measured, a focal length of the lens system may be adjusted to focus the camera.

Next, when the camera 20 is focused, the camera 20 may be vertically moved within a set movement distance range, starting to move from the current location of the camera 20, so as to acquire a plurality of images of the target to be measured. Referring to FIG. 2, the camera 20 is vertically moved within a distance range between Z1 and Z2 and Z3 to acquire a plurality of images of a target to be measured. Here, Z1 denotes a current location of the camera 20 when the camera 20 is focused. Z2 and Z3 denote the highest location to which the camera 20 may be lifted, and the lowest location to which the camera 20 may descend, respectively.

After the camera 20 is lifted to Z2, a plurality of images may be acquired while the camera 20 descends from Z2 to Z3. Alternatively, after the camera 20 descends to Z3, a plurality of images may be acquired while the camera 20 is lifted from Z3 to Z2. With a Z axis defined as an axis along which the camera 20 vertically moves, the camera 20 may be vertically moved by a Z axis driving device 50. In order to reduce an inspection time, the camera 20 may be a high-speed camera capable of high-speed photographing. The camera 20 may convert input light into an electric signal by the image sensor 21, such as a CCD, to output the electric signal to the control unit 40, which then generates images from the electric single.

The movement distance range for acquiring images may be set to be wider than the repeatability distance range of the automatic focusing module 30. Within the repeatability distance range, the camera generates the images with substantially same quality. The camera 20 is vertically moved within the movement distance range to photograph a plurality of frames, in which a photographing distance range, within which each image is taken by the camera, may be set to be narrower than the repeatability distance range of the automatic focusing module 30. For example, if repeatability distance range is from 0.025 μm to 0.03 μm, the movement distance range for acquiring images may be set to be about 0.01 μm, and a number of frames photographed within the region is set to be about 500, with a photographing distance range being 0.0002 μm.

Next, after an image with the highest definition is selected from the plurality of acquired images, the selected image is processed, and it is determined whether the target to be measured is defective or not. These operations may be performed by the control unit 40.

Among a plurality of images acquired by vertically moving the camera 20 within the set region, an image with the highest definition may be included. As a result, a form of a target may be accurately identified from the image with the highest definition, thereby enhancing accuracy of determining a defect in a target to be measured.

That is, even if a camera is automatically focused on a target to be measured, there may be an error in the automatic focus due to assembly tolerance of the automatic focusing module 30 itself, or substrate bending in the flat panel 10. As a result, accuracy may be reduced if an image acquired in such conditions is used to determine a defect in a target to be measured. However, according to an exemplary embodiment, after a camera is automatically focused, a plurality of images are acquired, among which an image with the highest definition is extracted to be used, such that a defect in a target to be measured may be determined with enhanced accuracy, even though there is an error in the automatic focus.

Further, there may be a limit to lowering repeatability of the automatic focus module 30. With resolution of the flat panel 10 becoming higher, there may be an error in a case where a target to be measured, for example pixel circuit patterns, is miniaturized, such that a line width is narrower than the repeatability of the automatic focus module 30. However, according to an exemplary embodiment, for the reasons set forth above, a line width of a fine circuit pattern may be measured with enhanced accuracy. In an experiment conducted by the inventors of the present disclosure, it was confirmed that in a case where repeatability of the automatic focus module 30 was from 0.025 μm to 0.03 μm, the repeatability was lowered in half to 0.011 μm to 0.015 μm by applying the method of the present disclosure, and repeatability may be controlled within a threefold range of a standard deviation, that is, within three-sigma (σ) limits.

Further, in order to acquire a plurality of images, the camera 20 may be vertically moved by a piezoelectric actuator. That is, the Z axis driving device 50 may include a piezoelectric actuator. The piezoelectric actuator refers to an actuator that generates displacement by inverse piezoelectric effect using expansive force and contractile force. The piezoelectric element may control minute displacement with high precision and high responsiveness, such that a plurality of images may be obtained while controlling vertical movement of the camera 20 with high speed and precision.

In addition, a target to be measured may be pixel circuit patterns formed in a flat panel 10. In this case, determining whether the target to be measured is defective or not may include measuring a line width and/or pattern width of a circuit pattern, and comparing the line width and pattern width to a reference value, to determine whether a circuit pattern is defective. Such process may be performed by the control unit 40. For example, if the flat panel 10 is a TFT LCD panel, a circuit pattern of a pixel may be an electrode line and a signal line of the TFT. By measuring a line width or a pattern width of the electrode line and the signal line, a defect may be determined.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims. Further, the above-described examples are for illustrative explanation of the present invention, and thus, the present invention is not limited thereto.

The invention claimed is:

1. A method for inspecting a flat panel, the method comprising:
    arranging a camera at a measurement location of the flat panel by horizontally moving at least one of the flat panel and the camera;
    automatically focusing the camera by using an automatic focusing module having a repeatability distance range on a target to be measured of the flat panel at the measurement location;
    acquiring a plurality of images of the target to be measured by vertically moving the focused camera upward or downward within a set movement distance range, wherein each of the plurality of images is taken by the camera within a photographing distance range;
    selecting an image with the highest definition among the plurality of acquired images to process the selected image; and
    determining whether the target to be measured is defective or not,
    wherein the set movement distance range for acquiring the plurality of images is greater than the repeatability distance range of the automatic focusing module, and the photographing distance range is smaller than the repeatability distance range of the automatic focusing module.

2. The method of claim 1, wherein the acquiring of the plurality of images comprises vertically moving the camera by a piezoelectric actuator.

3. The method of claim 1, wherein the target to be measured is a pixel circuit pattern disposed in the flat panel; and
    the determining whether the target to be measured is defective or not comprises measuring a line width and/or a pattern width of the circuit pattern of the selected image, and comparing the measured line width and/or the pattern width of the circuit pattern to a reference value to determine whether the circuit pattern is defective or not.

* * * * *